United States Patent
Reitz et al.

(10) Patent No.: US 6,358,946 B1
(45) Date of Patent: Mar. 19, 2002

(54) C-6 RING-SUBSTITUTED PYRIDO[1,2-A] BENZIMIDAZOLE DERIVATIVES USEFUL IN TREATING CENTRAL NERVOUS SYSTEM DISORDERS

(75) Inventors: Allen B. Reitz, Lansdale; Samuel O. Nortey, Elkins, both of PA (US); Pauline Sanfilippo, Flemington, NJ (US); Malcolm K. Scott, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/619,804

(22) Filed: Jul. 20, 2000

Related U.S. Application Data

(60) Provisional application No. 60/146,731, filed on Aug. 2, 1999.

(51) Int. Cl.[7] .................. C07D 471/04; C07D 235/00; C07D 221/00; A61K 31/437; A61P 25/00
(52) U.S. Cl. .................. 514/228.2; 546/19; 546/86; 514/278; 514/292; 514/233.2; 514/253.05; 544/126; 544/361; 544/58.6
(58) Field of Search .................. 546/19, 86; 514/278, 514/292, 253.03, 228.2, 233.2; 544/126, 361, 58.6

(56) References Cited

U.S. PATENT DOCUMENTS

| | | | |
|---|---|---|---|
| 5,521,200 A | 5/1996 | Ho et al. | 514/338 |
| 5,817,668 A | 10/1998 | Reitz et al. | 514/292 |
| 5,922,731 A | 7/1999 | Reitz et al. | 514/292 |
| 5,968,946 A | 10/1999 | Maryanoff et al. | 514/293 |

FOREIGN PATENT DOCUMENTS

| | | |
|---|---|---|
| RU | 1027166 | 9/1981 |
| WO | WO 99/40092 | 8/1999 |
| WO | WO 00/10973 | 3/2000 |

OTHER PUBLICATIONS

S. Ohta et al., Synthesis and Application of Imidazole Derivatives. Synthesis of Pyrido{1,2–a}Benzimidazolone Derivatives[1], Heterocycles vol. 32, No. 10, 1991, pp. 1923–1931.

Susumu Takada et al., Thienylpyrazoloquinolines: Potent Agonists and Inverse Agonists to Benzodiazepine Receptors, J. Med. Chem. 1988, vol. 31, pp. 1738–1745.

Michael Williams et al., CGS 20625, A Novel Pyrazolopyridine Anxiolytic, The Journal of Pharmacology and Experimental Therapeutics, Sep. 12, 1988, vol. 248 No. 1, pp. 89–96.

Shunsaka Ohta et al., Synthesis and Application of Imidazole Derivatives. Synthesis of Pyrrolo{1,2–A}Benzimidazoles..., Chem. Pharm. Bull. 1991, 39(11) pp. 2787–2792.

Samia M. Rida et al., Benzimidazole Condensed Ring Systems.1.Synthesis and Biological Investigation of Some Substituted Pyrido{1,2–a}Benzimidazoles, J. Heterocyclic Chem., vol. 25, 1988, pp. 1087–1093.

Farid S.G. Soliman et al., Synthesis of Substituted 3–Hydroxy–1H,5H–Pyrido{1,2–a}— Benzimidazol–1–Ones as Possible Antimicrobial and Antineoplastic Agents, Arch. Pharm. vol. 317, 1984, pp. 951–959.

*Primary Examiner*—Richard L. Raymond
*Assistant Examiner*—Hong Liu
(74) *Attorney, Agent, or Firm*—Mary Appollina

(57) ABSTRACT

A C-6 ring-substituted pyrido[1,2-a]benzimidazole derivative of the formula:

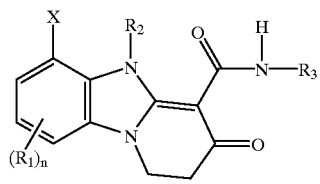

methods of preparation and pharmaceutical compositions containing a substituted pyrido[1,2-a]benzimidzole derivative as the active ingredient are disclosed. The substituted pyrido[1,2-a]benzimidazole derivatives are useful in the treatment of central nervous system disorders.

18 Claims, No Drawings

C-6 RING-SUBSTITUTED PYRIDO[1,2-A] BENZIMIDAZOLE DERIVATIVES USEFUL IN TREATING CENTRAL NERVOUS SYSTEM DISORDERS

CROSS REFERENCE TO RELATED APPLICATIONS

This application claims the benefit of U.S. Provisional Application 60/146731, filed on Aug. 2, 1999, which is incorporated by reference herein in its entirety.

FIELD OF THE INVENTION

This invention relates to a series of C-6-substituted pyrido [1,2-a]benzimidazole derivatives and to pharmaceutical compositions containing them. The compounds are ligands for the BZD site on GABA-A receptors and are thus useful for the treatment of disorders of the central nervous system.

BACKGROUND OF THE INVENTION

The gamma-aminobutyric acid-A (GABA-A receptor) is the most abundant inhibitory receptor in the brain of mammals. It is comprised of a heteropolymeric structure that forms a chloride ion channel, and bears multiple recognition sites for the binding of modulatory molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Smith and Olsen, Trends Pharm. Sci., 1995, 16, 162; Stephenson, Biochem. J., 1995, 310, 1). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. J. Med. Chem. 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. Arzneim.-Forsch./Drug Res. 1992, 42 (2a), 211; Haefely, W. et al., *Advances in Drug Research*, Academic Press, vol. 14, 985, pp. 165–322; Skolnick, P. et al. GABA and *Benzodiazepine Receptors*, Squires, R., Ed., 1987, pp. 99–102 and references cited therein.)

The benzodiazepines are a class of compounds which bind to the BZD receptor with high affinity. Most of the drugs in use are agonist-type ligands for the receptor. Such compounds are generally useful for their anticonvulsant, anxiolytic, sedative, and muscle relaxant effects. Antagonists of the BZD binding site are thus useful for the treatment of benzodiazepine drug overdose and inverse agonists are useful in managing alcoholism.

The present invention is concerned with novel compositions of matter and their use. Compounds having some structural similarity to those of the present invention are described in Rida, S. M. et al. *J. Het Chem.* 1988. 25, 1087; Soliman, F. S. G. et al. *Arch. Pharm.* 1984, 317, 951; Volovenko, Y. M. et al. U.S.S.R. Patent SU 1027166 (*Chem Abs.* 99(25) 212524t; Ohta, S. et al. *Heterocycles* 1991, 32, 1923; Ohta, S. et al. *Chem. Pharm. Bull.* 1991, 39, 2787. In addition, related compounds are disclosed in U.S. Pat Nos. 5,817,668, 5,817,668, 5,639,760, 5,521,200 and 5,922,731. The novel compounds differ from the prior art compounds in that they contain a ring substituent in the 6-position of the A ring.

DISCLOSURE OF THE INVENTION

The present invention is directed to compounds of the following formula:

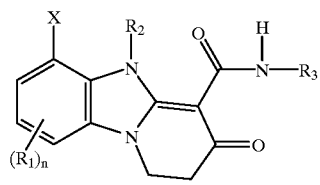

1 wherein $R_1$, $R_2$, $R_3$, X and n are as defined hereinafter. The compounds of Formula 1 are useful in treating central nervous system disorders. The compounds are ligands for the BZD binding site on GABA-A receptors and are thus useful as muscle relaxants, hypnotics/sedatives including sleep-aids, anxiolytics, antidepressants, anticonvulsants/ antiepileptics, anti-inebriants, and antidotes for drug overdose.

The present invention also comprises pharmaceutical compositions containing one or more of the compounds of formula 1 as the active ingredient and methods for the treatment of disorders to the central nervous system including convulsions such as epileptic seizures, anxiety, depression, muscular spasms, sleep disorders, attention deficit hyperactivity disorder (ADHD) and benzodiazepine overdoses.

DETAILED DESCRIPTION OF THE INVENTION

More particularly, the present invention is directed to compounds of the general formula:

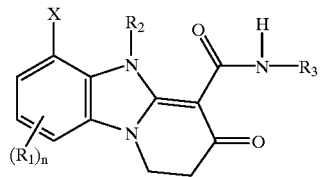

1 wherein:

$R_1$ is independently selected from the group consisting of hydrogen; $C_{1-8}$alkyl (including $C_{1-8}$ straight chain alkyl and $C_{3-8}$ branched chain alkyl); halogen; perfluoro$C_{1-4}$alkyl; hydroxy; $C_{1-4}$alkoxy; amino; di($C_{1-4}$alkyl)amino; amino$C_{1-4}$alkylamino; nitro; $C_{1-4}$alkoxycarbonyl; and $C_{1-4}$alkylthio; There may be up to three independent $R_1$ substituents on the ring (n=1–3); $R_1$ is preferably hydrogen, $C_{1-8}$alkyl, halogen or $C_{1-4}$alkoxy;

$R_2$ is selected from the group consisting of hydrogen; $C_{1-6}$ alkyl (including $C_{1-6}$ straight chain alkyl and $C_{3-6}$ branched chain alkyl); aralkyl; heteroaryl($C_14$)alkyl; $(R_4)_2N(CH_2)_p$ wherein $R_4$ is the same or different and is independently selected from H, $C_{1-4}$alkyl, aralkyl, aryl or substituted aryl wherein the substituents are independently selected from $C_{1-4}$alkyl, $C_{1-4}$alkoxy, nitro, amino or halo, and p is 1–5; or $R_4$ together with the nitrogen to which they are attached may form a heterocyclic group selected from piperidinyl, pyrrolidinyl, morpholinyl, thiomorpholinyl, piperazinyl, pyrazolyl, triazolyl, indolyl, indolinyl, imidazolyl, benzimidazolyl, pyrrolyl or indazolyl, preferably morpholinyl, piperidinyl or pyrrolidinyl; $R_5O(CH_2)_p$ wherein $R_5$ is selected from $C_{1-4}$alkyl, aralkyl, aryl or substituted aryl wherein the substituents are independently selected from $C_{1-4}$alkyl, $C_{1-4}$alkoxy, nitro, amino or halo and p is 1–5; and $R_5S(CH_2)_p$; wherein $R_5$ and p are as defined above; $R_2$ is preferably H or $C_{1-6}$alkyl;

$R_3$ is independently selected from the group consisting of aryl; substituted aryl, wherein the substituents are selected from $C_{1-8}$alkyl, halo, perfluoro$C_{1-4}$alkyl, hydroxy, $C_{1-4}$alkoxy, amino, di($C_{1-4}$alkyl)amino, $C_{1-4}$alkoxycarbonyl, amino$C_{2-6}$alkoxy, $C_{1-8}$alkylamino$C_{2-6}$alkoxy, di($C_{1-8}$alkyl)amino$C_{2-6}$alkoxy, or $C_{1-4}$alkylthio; a heteroaryl group selected from pyridyl; thiazolyl; thiophenyl; furyl; indolyl; imidazolyl; benzothiophenyl; pyridazinyl; pyrimidinyl; indolyl; indolinyl; quinolinyl; indazolyl; benzofuryl; triazinyl; pyrazinyl; isoquinolinyl; isoxazolyl; thiadiazolyl; benzothiazolyl; triazolyl; or benzotriazolyl; a substituted heteroaryl group wherein the substituent is selected from oxo, halo, perfluoro$C_{1-4}$alkyl, nitro, amino, $C_{1-4}$alkylthio, $C_{1-4}$alkoxy, $C_{1-4}$alkylamino, di($C_{1-4}$)alkylamino, carboxy or $C_{1-4}$alkoxycarbonyl; and cycloalkyl having 3-8 carbon atoms; $R_3$ is preferably aryl, haloaryl, $C_{1-4}$alkoxyaryl or heteroaryl;

X is a heterocyclic or carbocyclic ring selected from the group consisting of piperidinyl, pyrrolidinyl, morpholinyl, thiomorpholinyl, piperazinyl, imidazolyl, pyrazolyl, pyridinyl, pyrazinyl, pyrimidinyl, pyridazinyl, thiazolyl, isothiazolyl, oxazolyl, isoxazolyl, oxazolinyl, triazolyl, tetrazolyl, oxadiazolyl, dioxaazaspirodecanyl, thiadiazolyl, purinyl, benzimidazolyl, benzothiophenyl, benzothiazolyl, indolyl; cyclo($C_{3-8}$)alkyl; phenyl; and naphthyl; a substituted heterocyclic, carbocyclic, or aryl ring wherein the substituents are independently selected from $C_{1-8}$alkyl (including $C_{1-8}$ straight chain alkyl and $C_{3-8}$ branched chain alkyl), halogen, perfluoro$C_{1-4}$alkyl, hydroxy, amino, nitro, oxo, $C_{1-4}$alkoxy, $C_{1-4}$alkylamino, di($C_{1-4}$alkyl)amino, $C_{1-4}$alkoxycarbonyl, $C_{1-4}$alkoxy$C_{1-4}$alkylcarbonyl, aryl, substituted aryl wherein the substituents are independently selected from $C_{1-4}$alkyl, $C_{1-4}$alkoxy, nitro, amino, or halo; heteroaryl and $C_{1-4}$alkylthio; preferably, X is a heterocyclic ring;

and pharmaceutically acceptable salts thereof.

As used herein unless otherwise noted the terms "alkyl" and "alkoxy" whether used alone or as part of a substituent group, include straight and branched chains having 1–8 carbon atoms. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. The term "aryl" is intended to include phenyl and naphthyl. The term "halo", unless otherwise indicated, includes bromo, chloro, fluoro and iodo. The term "cycloalkyl" is intended to include cycloalkyl groups having 3–8 carbon atoms. The term "aralkyl" is intended to include an aryl group attached to a $C_{1-8}$alkyl group, preferably a $C_{1-4}$alkyl group (e.g., benzyl, phenylethyl).

The term "heteroaryl" is intended to include an aromatic ring containing at least one heteroatom selected from sulfur, oxygen or nitrogen, optionally containing one to three additional heteroatoms independently selected from sulfur, oxygen ot nitrogen, such as, but not limited to, pyridyl, thiazolyl, thiophenyl, furyl, indolyl, imidazolyl, benzothiophenyl, pyridazinyl, pyrimidinyl, indolinyl, quinolinyl, indazolyl, benzofuryl, isoquinolinyl, triazinyl, pyrazinyl, isoxazolyl, thiadiazolyl, benzothiazolyl, triazolyl, benzotriazolyl, oxazolyl, and the like.

The term "heterocyclic ring" is intended to include a saturated, partially unsaturated, partially aromatic or aromatic ring structure containing at least one heteroatom selected from sulfur, oxygen or nitrogen, optionally containing one to three additional heteroatoms independently selected from sulfur, oxygen or nitrogen, such as, but not limited to piperidinyl, pyrrolidinyl, morpholinyl, thiomorpholinyl, piperazinyl, indolinyl, pyrazolyl, triazolyl, indolyl, benzimidazolyl, pyrrolyl, indazolyl, pyridinyl, pyrazinyl, pyrimidinyl, pyridazinyl, thiazolyl, isothiazolyl, oxazolyl, dioxaazaspirodecanyl, thiadiazolyl, purinyl, benzimidazolyl, benzothiphenyl, benzothiazolyl, indolyl, and the like. The term "carbocyclic ring" is intended to include saturated, partially unsaturated, partially aromatic or aromatic ring structure such as, but not limited to cyclopropyl, cyclobutyl, cyclopentyl, cyclohexyl, cycloheptyl, cyclooctyl, phenyl, naphthyl, and the like.

When a particular group (e.g., aryl, heteroaryl) is substituted, that group may have one or more substituents (preferably, one to five, more preferably, one to three, most preferably, one or two substituents) independently selected from the listed substituents. With reference to substituents, the term "independently" means that when more than one of such substituent is possible, such substituents may be the same or different from each other.

As used herein, the abbreviation "Ph" shall mean phenyl, "Me" shall mean methyl, "Et" shall mean ethyl, "MeOH" shall mean methanol, "EtOH" shall mean ethanol and "EtOAc" shall mean ethyl acetate.

Those compounds of the present invention which contain a basic moiety can be converted to the corresponding acid addition salts by techniques known to those skilled in the art. Suitable acids which can be employed for this purpose include hydrochloric, hydrobromic, hydriodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. In general, the acid addition salts can be prepared by reacting the free base of compounds of formula 1 with the acid and isolating the salt.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention.

The compounds of Formula 1 are prepared as outlined in the following

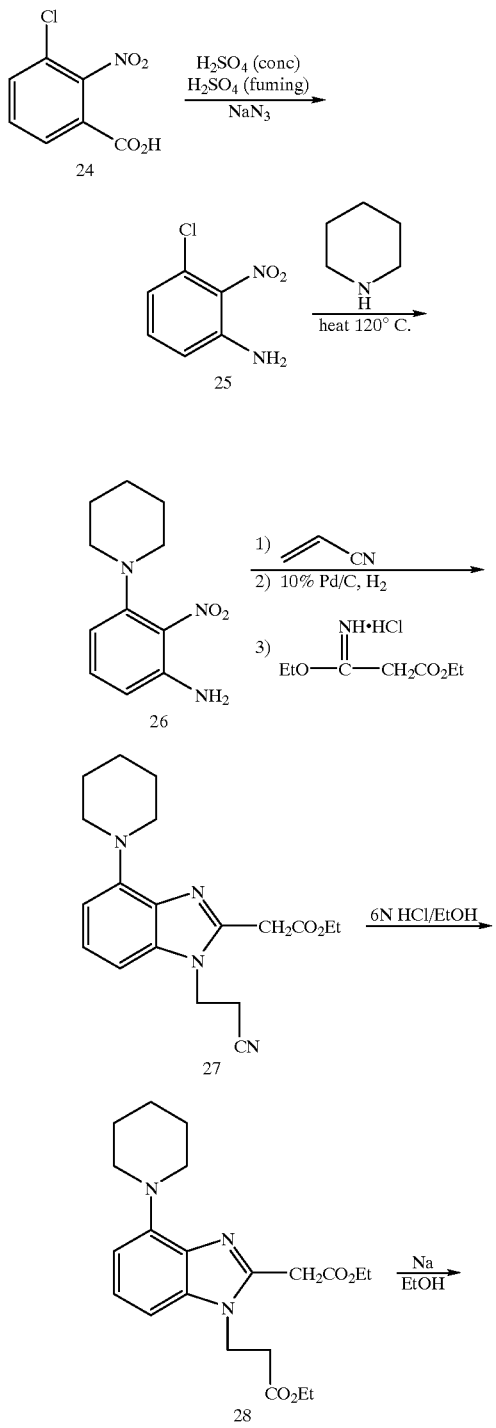

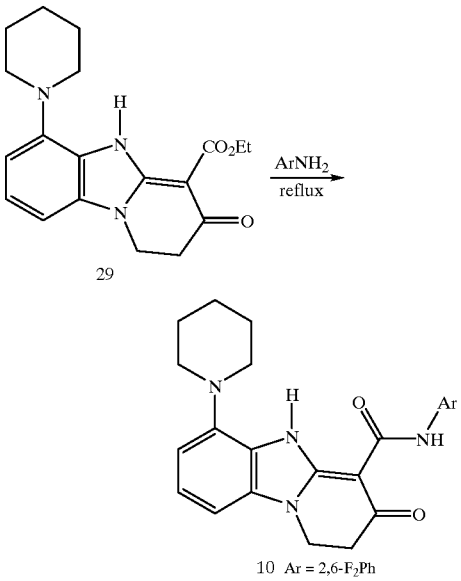

More specifically, an appropriately substituted benzoic acid (24) was treated with sodium azide, or under other suitable conditions known to promote a Curtius type rearrangement, to form a substituted nitro aniline (25). Treatment of the nitro aniline (25) with an appropriate nucleophile such as, for example, piperidine, imidazole, thiazole or morpholine, gives the chlorine displaced nitroaniline product (26 in the case of piperidine). The reaction is generally carried out at elevated temperatures (100–125° C.). Alternatively, carbon-carbon bond formation can be achieved by suitable protection of the aniline nitrogen of 25 followed by organometallic coupling reactions, e.g. organo-copper coupling to incorporate phenyl substitution and Grignard reagent formation followed by condensation with ketones, elimination, and reduction for saturated carbocyclics. In the case of piperidine substitution, nitroaniline 26 is reacted with acrylonitrile in a suitable solvent such as dioxane, tetrahydrofuran or chloroform, for example, at a temperature ranging from room temperature to about 40° C., to incorporate the cyanoalkyl group. The resulting material is then reacted with hydrogen in the presence of a catalyst, such as Pd/C, in a solvent such as ethanol, for example, to form an amino nitrile, which is then reacted with ethoxy-carbonylacetimidate hydrochloride under reflux conditions to form 1-cyanoethyl-2-(ethoxycarbonylmethyl) derivative 27. The cyanoalkyl derivative (27) is then hydrolyzed with ethanolic hydrochloric acid to form the 1-(ethoxycarbonylethyl)-2-(ethoxycarbonylmethyl) derivative (28). Reaction of the diester (28) with a base such as, for example, sodium ethoxide, yields the corresponding ethyl ester derivative (29). At this stage the N-5 nitrogen can be further substituted under basic conditions for those compounds of the invention where $R_2$ is other than hydrogen. Reaction of the ethyl ester (29) with an amine such as, for example, 2,6-difluoroaniline, in a suitable solvent such as xylene, for example, at reflux temperatures yields the substituted benzimidazole-4-carboxamine derivative (10).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 0.5 to about 20 mg of the active ingredient, although other unit dosages may be employed.

In therapeutic use in treating disorders of the central nervous system in mammals, the compounds of this invention may be administered in an amount of from about 0.01 to 5 mg/kg per day. In therapeutic use as an anxiolytic, the compounds of the invention may be administered in an amount from about 0.01 to 5 mg/kg per day. In therapeutic use as an anticonvulsant/antiepileptic, the compounds of the invention may be administered in an amount from about 0.01 to 5 mg/kg per day. In therapeutic use as an agent for treating benzodiazepine overdoses, the compounds of the invention may be administered in an amount from about 0.01 to 5 mg/kg per day. In therapeutic use as a sedative/hypnotic, a therapeutically effective amount is from about 0.01 to 5 mg/kg per day. As a muscle relaxant about 0.01 to 5 mg/kg per day of the compounds of this invention may be used. Determination of optimum dosages and frequency of administration for a particular disease state or disorder is within the experimental capability of one skilled in the art.

The following examples describe the invention in greater detail and are intended to illustrate the invention, but not to limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data are reported in parts per million downfield from tetramethylsilane. Mass spectra data are reported in mass/charge (m/z) units. Unless otherwise noted, the materials used in the examples were obtained from readily available commercial sources or synthesized by standard methods known to those skilled in the art.

EXAMPLE 1

Pyrido[1,2-a]benzimidazole-4-carboxamide, N-(2,6-difluorophenyl)-1,2,3,5-tetrahydro-3-oxo-6-piperidinyl)-(#10)

A. Preparation of 3-(1-piperidinyl)-2-nitroaniline (26). Compound (25) was prepared from compound (24) by the method described in W. N. White and J. R. Klink *J. Org. Chem.* 1977, 42, 166. A mixture of 5 g (0.03 mol) of 3-chloro-2-nitroaniline (25) and 15 mL of piperidine was heated to 120° C. for 1.5 h, the mixture was cooled, and excess piperidine was evaporated off under reduced pressure while maintaining the water bath temperature below 50° C. After cooling, the residue was redissolved in methylene chloride, washed with water and brine, dried ($Na_2SO_4$), and concentrated to provide 26 as a brown syrup, which was stored under argon. MS m/z=222(M+H). 300-MHz $^1$H NMR ($CDCl_3$) δ 7.10 (t, 1H), 6.30–6.40 (m, 2H), 4.80 (s, broad, 2H), 2.90 (m, 4H), 1.55–1.70 (m, 4H), 1.49–1.54 (m, 2H). Compound 26 was used in the next step without further purification.

B. 1-(2-Cyanoethyl)-2-(ethoxycarbonylmethyl)-4-(1-piperidinyl)benzimidazole (27). A 40% solution of benzyltrimethylammonium hydroxide in MeOH (2.6 mL) was added to a solution of 3-(1-piperidinyl)-2-nitroaniline 26 (6.4 g, 0.03 mol) in dioxane (70 mL) at room temperature. Acrylonitrile (3.0 g, 0.06 mol) was added dropwise to the reaction mixture, and the resulting exotherm was controlled by means of an external ice bath so that the temperature did not increase past 35–40° C. The solution was then stirred at room temperature for 24 h and concentrated under vacuum, while maintaining the water-bath temperature below 50° C., to give a dark yellow syrup (10.0 g). This air sensitive cyanoalkyl compound was immediately dissolved in 200 mL of ethanol and 30 mL of THF (tetrahydrofuran), and the resultant solution was treated with 10% Pd/C (1.5 g), placed in a Parr bottle, and hydrogenated at 50–60 psig for 34 h. The resultant aminonitrile was treated under inert atmosphere with ethoxycarbonylacetimidate hydrochloride (5.8 g, 0.03 mol), heated under reflux for 12 h, and allowed to cool to room temperature overnight. The mixture was filtered and the filtrate concentrated in vacuo to provide a gray residue, which was redissolved in methylene chloride, washed once with water, once with brine, dried ($Na_2SO_4$), filtered, and concentrated in vacuo. The residue was purified on a Waters prep-500 HPLC (ethylacetate:hexane, 1:1) to give cyanoalkyl benzimidazole 27 as a pale yellow syrup. MS m/z=341 (M+H). 300-MHz $^1$H NMR ($CDCl_3$) δ 7.50 (t, 1H), 6.80 (d, 1H), 6.65 (d, 1H), 4.40 (t, 2H, CH$_2$N), 4.20 (q, 2H, CH$_2$CH$_3$), 4.05 (s, 2H, CH$_2$CO$_2$), 3.50 (m, 4H), 2.90 (t, 2H), 1.75 (m, 4H), 1.65 (m, 2H), 1.3 (t, 3H).

C. 1-[2-(Ethoxycarbonyl)ethyl]-2-(ethoxycarbonyl methyl)-4-(1-piperidinyl)benzimidazole (28). Cyanoalkyl derivative 27 (5.02 g, 0.015 mol) was treated with 6N ethanolic HCl (60 mL) and the mixture was stirred under argon for 14 h. The solution was concentrated in vacuo to a syrup, which was treated with ice and water, neutralized with 15% NaOH (pH=8–10), and extracted into methylene chloride. The extracts were washed with brine, dried ($Na_2SO_4$), filtered, and concentrated in vacuo to give desired diester 28 as a light brown solid: mp 82–85° C. MS m/z=388 (M+H). 300-MHz $^1$H NMR ($CDCl_3$) δ 7.5 (t, 1H), 6.80 (d, 1H), 6.65 (d, 1H), 4.45 (t, 2H, CH$_2$N), 4.18–4.25 (q, 2H), 4.10 (s, 2H, CH$_2$CO$_2$), 4.05–4.14 (q, 2H), 3.45 (m, 4H), 2.85 (t, 2H), 1.75 (m, 4H), 1.65 (m, 2H), 1.24–1.31 (t, 3H), 1.12–1.23 (t, 3H).

D. Pyrido[1,2-a]benzimidazole-4-ethoxycarbonyl, 1,2,3,5-tetrahydro-3-oxo-6-(1-piperidinyl)-(29). Sodium (1.18 g, 0.05 mol) was added to a stirred solution of absolute EtOH (60 mL) under argon until all solids dissolved. Diester derivative 28 (4.90 g, 0.013 mol) in 10 mL of ethanol was added dropwise to the sodium ethoxide solution thus prepared, and the mixture was stirred for 24 h. It was then concentrated in vacuo to a yellow solid, which was suspended in water (20 mL) and the pH was then adjusted to 8–10 by addition of 1N HCl. The resulting precipitate was filtered and dried under vacuum at 40° C. to give derivative 29 as a solid: mp 206–208° C. MS m/z=342 (M+H). 300-MHz 1H NMR (CDCl$_3$) δ 11.00 (s, broad, 1H), 6.90 (t, 1H), 6.60 (d, 1H), 6.55 (d, 1H), 4.05 (q, 2H), 3.90 (t, 2H), 2.75 (m, 4H), 2.50 (t, 2H), 1.50 (m, 4H), 1.35 (m 2H), 1.05 (t, 3H).

E. Pyrido[1,2-a]benzimidazole-4-carboxamide, N-(2,6-difluorophenyl)-1,2,3,5-tetrahydro-3-oxo-6-(1-piperidinyl)-(10). Ethyl ester 29 (7.10 g, 0.02 mol) and 2,6-difluoroaniline (7.5 g, 0.058 mol) were combined in xylenes (180 mL) and heated to reflux for 6 h. The resulting solution was concentrated in vacuo to give 10 (8.5 g) as a light brown solid which was treated with ethanolic HCl solution to afford the monohydrochloride salt. This material was recrystallized from a mixture of methylene chloride and 95% ethanol to give the title compound (10) as a light yellow solid: mp 240–241° C. MS m/z=425 (M+H). 300-MHz $^1$H NMR (DMSO-d$_6$) δ 11.85 (s, br, 1H), 11.15 (s, 1H), 7.25–7.39 (m, 3H), 7.15–7.24 (m, 2H), 7.00 (m, 1H), 4.30 (t, 2H), 3.00–3.20 (m, 4H), 2.80 (t, 2H), 1.70–1.80 (m, 4H), 1.55–1.65 (m, 2H). Anal. calc'd for C$_{23}$H$_{22}$F$_2$N$_4$O$_2$.HCl.0.5H$_2$O: C, 58.79; H, 5.15; Cl, 7.54; N, 11.92; KF, 1.92. Found: C, 58.99; H, 4.94; Cl, 7.19; N, 11.93; KF, 0.88.

Compounds 9 and 11 (see Table 1) were prepared in a similar manner using either 2-fluoroaniline or 4-methoxyaniline, respectively, instead of 2,6-difluoroaniline in step E. Compound 4 was prepared in a similar manner using morpholine instead of piperidine in step A. Compound 14 was prepared in a similar manner using thiomorpholine instead of piperidine in step A and 2-fluoroaniline instead of 2,6-difluoroaniline in step E. Compounds 3, 7, and 8 were prepared in a similar manner using morpholine instead of piperidine in step A and either 2-fluoroaniline, 4-methoxyaniline, or 3-methoxyaniline, respectively, instead of 2,6-difluoroaniline in step E. Compound 5 was prepared in a similar manner using 1-(2-methoxyphenyl)piperazin-4-yl instead of piperidine in step A. Compound 6 was prepared in a similar manner using 1-(2-methoxyphenyl)piperazin-4-yl instead of piperidine in step A and 2-fluoroaniline instead of 2,6-difluoroaniline in step E.

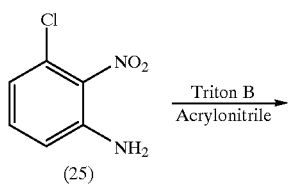

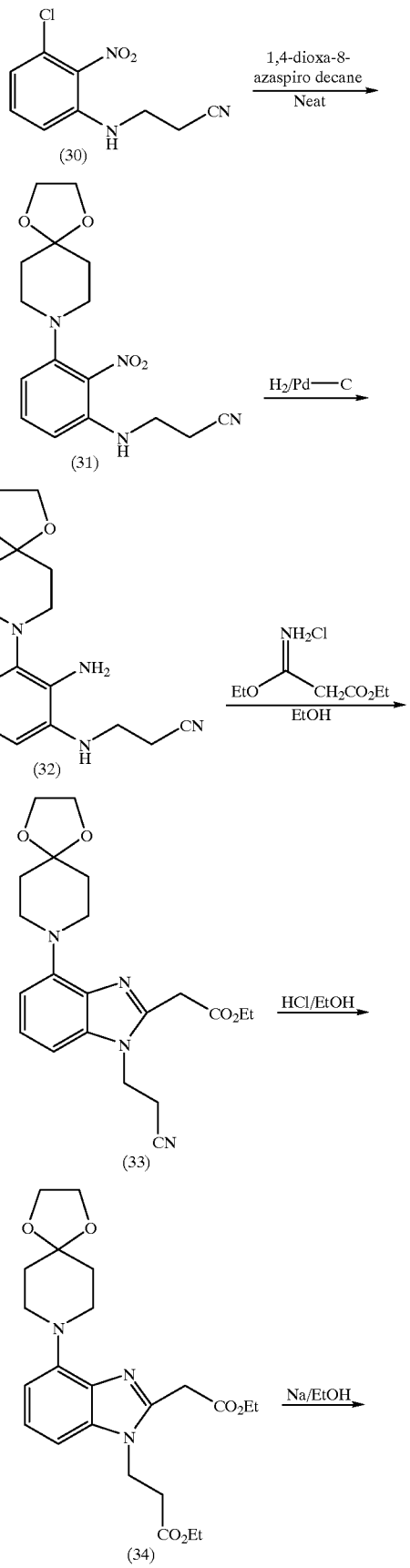

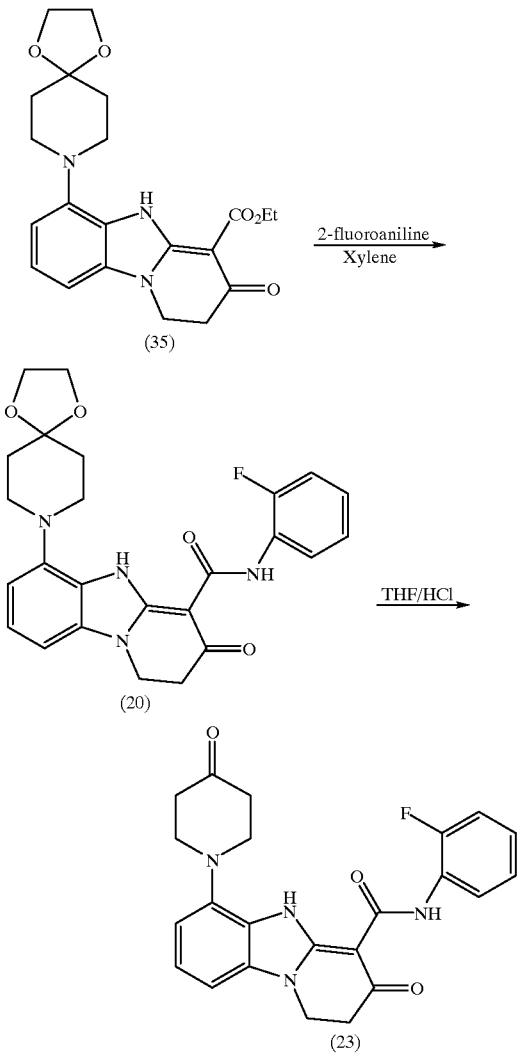

EXAMPLE 2

Pyrido[1,2-a]benzimidazole-4-carboxamide, N-2-fluorophenyl-1,2,3,5-tetrahydro-oxo-6-[8-(1,4-dioxa-8-azaspiro[4,5]decanyl)]-(#20)

A. 3-Chloro-2-nitro-N-(2-cyanoethyl)aniline (30). Triton B (0.04 ml, 4 mol %) was added to a solution of 25 (1.0 gm, 5.8 mmol) in dioxane (20 ml). After cooling to 0° C., acrylonitrile (1.53 ml, 23 mmol) was added. The resulting solution was stirred at room temperature overnight. The solvent was vacuum evaporated and the residue was subjected to column chromatography (CHCl$_3$) to give 30. MS MH$^+$ 226.0. $^1$H NMR (300 MHz, CDCl$_3$) δ 2.69 (t, 2H, J=6.86 MHz, J=6.78 MHz), 3.62 (t, 2H, J=5.99 MHz, J=6.15 MHz), 5.85 (m, 1H, NH), 6.74 (d, 1H, J=8.57 MHz), 6.87 (d, 1H, J=8.57 MHz), 7.28 (t, 1H, J=8.57 MHz, J=8.57 MHz).

B. 3-[8-(1,4-Dioxa-8-azaspiro[4,5]decanyl)]-2-nitro-N-(2-cyanoethyl)aniline (31). Compound 30 (23 gm, 0.1 mol) and 1,4-dioxa-8-azaspiro[4,5]decane (35 gm, 0.24 mol) was heated to 80° C. overnight. The resulting mixture was separated by column chromatography (1:4 EtOAc/hexane) to give 31. MS MH$^+$ 333.1. $^1$H NMR (300 MHz, CDCl$_3$) δ 1.83 (t, 4H, J=6.86 MHz, J=7.71 MHz), 2.67 (t, 2H, J=8.57 MHz, J=8.57 MHz), 3.14 (t, 4H, J=4.28 MHz, J=5.23 MHz), 3.58 (m, 2H), 3.99 (s, 4H), 6.05 (m, 1H, NH), 6.33 (d, 1H, J=9.0 MHz), 6.46 (d, 1H, J=9.1 MHz), 7.22 (t,1H, J=9.0 MHz, J=9.1 MHz).

C. 3-[8-(1,4-Dioxa-8-azaspiro[4,5]decanyl)]-2-amino-N-(2-cyanoethyl)aniline (32). A solution of 31 (11.1 gm) in EtOAc (50 mL) was placed in a hydrogenation bottle and the bottle was flushed with nitrogen. Palladium (10% Pd/C, 2.2 gm) was added and the mixture was subjected to hydrogenation under 53 psig for 2 hrs. The catalyst was filtered and the solvent was evaporated under vacuum to give 32. MS MH$^+$ 303.1. $^1$H NMR (300 MHz, CD$_3$OD) δ 1.86 (m, 4H), 2.72 (t, 2H, J=7.71 MHz, J=7.81 MHz), 2.88 (m, 4H), 2.95 (t, 2H, J=7.71 MHz, J=7.81 MHz), 3.9 (s, 4H), 6.05 (m, 1H, NH), 6.46 (d, 1H, J=9.0 MHz), 6.59 (d, 1H, J=8.57 MHz), 6.67 (t, 1H, J=8.57 MHz, J=9.0 MHz).

D. 1-(2-Cyanoethyl)-2-(ethoxycarbonylmethyl)-4-[8-(1,4-dioxa-8-azaspiro[4,5]decanyl)]benzimidazole (33). A solution of 32 (7.5 gm, 0.025 mol), ethyl ethoxycarbonylacetimidate (14.6 gm, 0.075 mol) in EtOH (100 mL) was refluxed overnight. The solvent was evaporated under vacuum and the mixture was purified by column chromatography (1:3 EtOAc:hexane) to give 33. MS MH$^+$ 399.0. $^1$H NMR (300 MHz, CDCl$_3$) δ 1.21–1.30 (m, 3H), 1.55 (s, 2H), 1.97 (m, 4H), 2.95 (t, 1H, J=7.7 MHz, J=7.7 MHz), 3.63 (m, 4H), 4.03 (s, 4H), 4.20 (q, 2H), 4.46 (t, 2H, J=8.57 MHz, J=7.7 MHz), 6.69 (d, 1H, J=9.0 MHz), 6.85 (d, 1H, J=9.43 MHz), 7.17 (t,1H, J=9.43 MHz, J=9.0 MHz).

E. 1-[-2-(Ethoxycarbonyl)ethyl]-2-(ethoxycarbonylmethyl)-4-[8-(1,4-dioxa-8-azaspiro[4,5]decanyl)]benzimidazole (34). A solution of 33 (7.5 gm, 0.019 mol) in 1N HCl/EtOH (120 mL) was refluxed for 2 hrs. The solution was then added to water (20 mL) and extracted with EtOAc (100 mL). The solvent was dried with sodium sulfate and evaporated under vacuum to give 34. The crude product was used in the next reaction without further purification. MS MH$^+$ 446.6. $^1$H NMR (300 MHz, CDCl$_3$) δ 1.15–1.25 (m, 6H), 1.98 (m, 4H), 2.06 (s, 2H), 2.87 (t, 2H), 3.63 (m, 4H), 4.0 (s, 4H), 4.05–4.15 (m, 4H), 4.41 (t, 2H, J=8.14 MHz, J=8.57 MHz), 6.65 (d, 1H, J=8.51 MHz), 6.89 (d, 1H, J=8.57 MHz), 7.14 (t, 1H, J=8.51 MHz, J=8.57 MHz).

F. Pyrido[1,2-a]benzimidazole-4-ethoxycarbonyl, 1,2,3,5-tetrahydro-3-oxo-6-[8-(1,4-dioxa-8-azaspiro[4,5]decanyl)]-(35). A solution of 34 (3.85 gm, 0.0086 mol) in EtOH (20 mL) was added to a solution of sodium (0.37 gm, 0.016 mol) in EtOH (50 mL) under room temperature. The mixture was stirred overnight before the pH was adjusted to 7–8 by adding dropwise 1N HCl in EtOH. The solvent was evaporated under vacuum and the residue was subjected to column chromatography (EtOAc) to give 35. MS MH$^+$ 399.7. $^1$H NMR (300 MHz, CD$_3$OD) δ 1.48 (t, 3H, J=8.57 MHz, J=6.89 MHz), 1.95 (m, 4H), 2.80 (t, 2H, J=8.57 MHz, J=7.7 MHz), 3.20 (m, 4H), 4.0 (s, 4H), 4.20–4.32 (m, 4H), 6.96 (d, 1H, J=7.71 MHz), 7.13 (d, 1H, J=8.57 MHz), 7.27 (t,1H, J=8.57 MHz, J=7.71 MHz).

G. Pyrido[1,2-a]benzimidazole-4-carboxamide, N-2-fluorophenyl-1,2,3,5-tetrahydro-3-oxo-6-[8-(1,4-dioxa-8-azaspiro[4,5]decanyl)]-(20). A solution of 35 (2.0 gm, 6.46 mmol) and 2-fluoroaniline (1.1 ml, 19 mmol) in xylene (50 mL) was refluxed overnight. The reaction mixture was then cooled to room temperature and the product precipitated. The crude solid was filtered and the product was purified by column chromatography (1:3 EtOAc/hexane) to give 20. MS MH$^+$ 465.0. $^1$H NMR (300 MHz, CDCl$_3$) δ 2.0 (m, 4H), 2.94 (t, 2H, J=8.5 MHz, J=7.73 MHz), 3.23 (m, 4H), 4.0 (s, 4H), 4.18 (t,2H, J=8.21 MHz, J=7.99 MHz), 6.88 (m, 2H), 7.0 (m, 1H), 7.08 (m, 2H), 7.21 (t,1H, J=8.57 MHz, J=7.71 MHz), 8.44 (t,1H, J=8.71 MHz, J=9.0 MHz). Anal. calc'd for $C_{25}H_{24}N_4O_4F \cdot 0.9\ HCl \cdot 0.1\ H_2O$: C, 60.16; H, 5.27; N, 11.23; Cl, 7.10. Found C, 60.76; H, 4,83; N, 11.53; Cl, 7.08.

EXAMPLE 3

Pyrido[1,2-a]benzimidazole-4-carboxamide, N-2-fluorophenyl-1,2,3,5-tetrahydro-3-oxo-1-(4-oxopiperidinyl)-(#23)

A solution of 20 (0.4 gm) in THF(5 mL) and 1N HCl in water (5 mL) was refluxed for 2 hrs. The solution was then added to water (10 mL) and the resultant mixture was extracted with EtOAc (50 mL). The solvent was dried with sodium sulfate and evaporated under vacuum to give 23 as a crude oil which was purified by column chromatography (1:3 EtOAc/hexane) to afford 23. MS MH$^+$ 421.2. $^1$H NMR (300 MHz, CDCl$_3$) δ 2.66 (t, 4H, J=5.14 MHz, J=6.0 MHz), 2.89 (t, 2H, J=6.85 MHz, J=6.0 MHz), 3.41 (t, 4H, J=4.71 MHz, J=5.57 MHz), 4.14 (t,2H, J=7.28 MHz, J=7.71 MHz), 6.8–7.2 (m, 6H), 8.34 (t,1H, J=6.86 MHz, J=7.71 MHz), 11.82 (s, 1H, NH), 12.21 (s, 1H, NH). Anal. calc'd for $C_{23}H_{21}N_4O_3F \cdot 0.4\ HCl \cdot 0.5\ H_2O$: C, 62.23; H, 5.08; N, 12.62; F, 4.28 Cl, 3.29. Found: C, 62.27; H, 5.13; N, 12.48; F, 4.40; Cl, 2.76.

EXAMPLE 4

Pyrido[1,2-a]benzimidazole-4-carboxamide, N-2-fluorophenyl-1,2,3-trihydro-3-oxo-5-methyl-6-[8-(1,4-dioxa-8-azaspiro[4,6]decanyl)]-(#21)

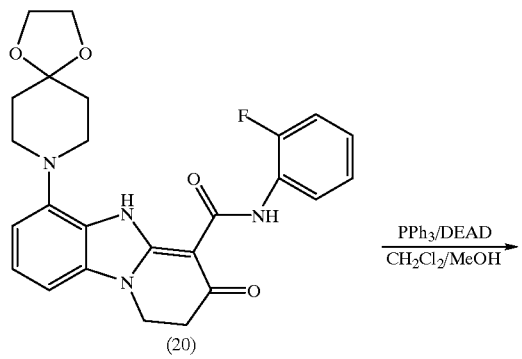

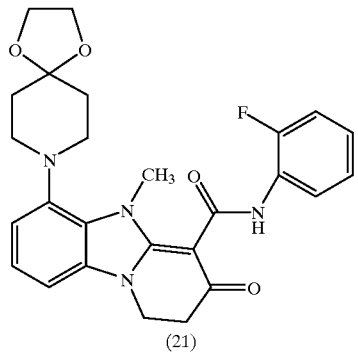

MeOH(0.04 mL, 1.1 mmol) was added to a solution of 20 (0.25 gm, 0.538 mmol), triphenylphosphine (Ph$_3$P) (0.42 gm, 1.6 mmol), diethylazodicarboxylate (DEAD) (0.25 ml, 1.6 mmol) in CH$_2$Cl$_2$ (5 mL). The resultant solution was then stirred at room temperature overnight. The solvent was evaporated by vacuum, and the crude product was purified by chromatography to isolate 21. MS MH$^+$ 479.0. $^1$H NMR (300 MHz, CDCl$_3$) δ 1.85–2.05 (m, 4H), 2.80 (t, 2H, J=6.42 MHz, J=7.28 MHz), 2.97–3.05 (m, 2H), 3.29–3.47 (m, 2H), 4.02 (s, 4H), 4.05 (s, 3H), 4.15 (m, 2H)$_7$ 6.95 (t, 3H, J=8.14 MHz, J=7.71 MHz), 7.08 (m, 2H), 7.26 (m, 2H), 8.48 (t, IH, J=8.14 MHz, J=8.57 MHz), 11.96 (s, 1H, NH). Anal. calc'd for $C_{26}H_{27}N_4O_4F \cdot 1.8\ HCl$: C, 54.47; H, 5.06; N, 9.66; F. 3.28; Cl, 16.50. Found: C, 54.45; H, 4.64; N$_7$ 9.47; F, 3.79; Cl, 16.63.

Compounds 12, 15, 16, and 18 were prepared in a similar manner starting from 3, 14, 17, and 9, respectively, instead of 20.

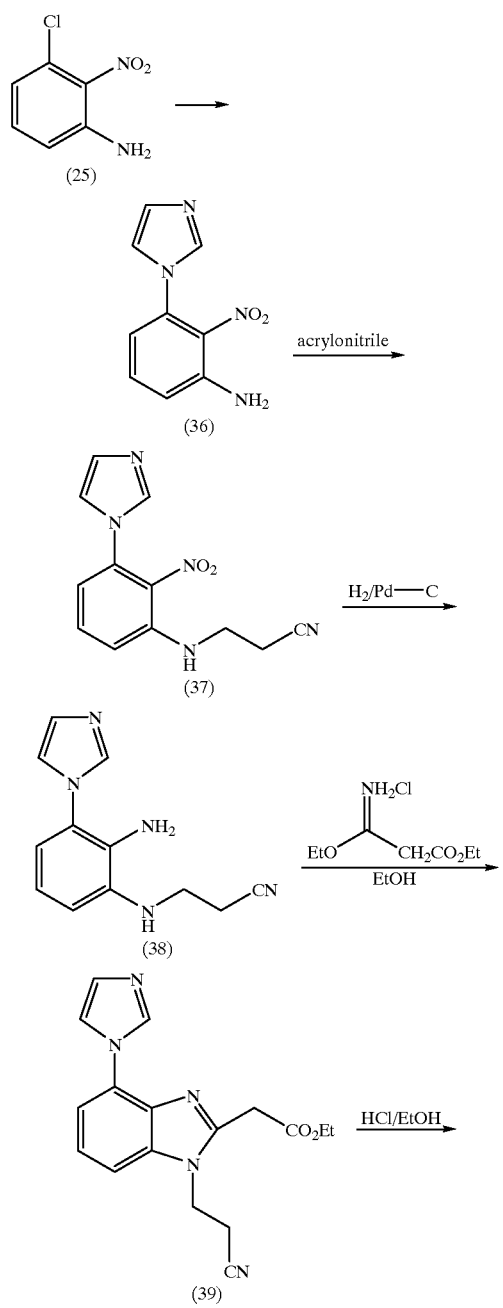

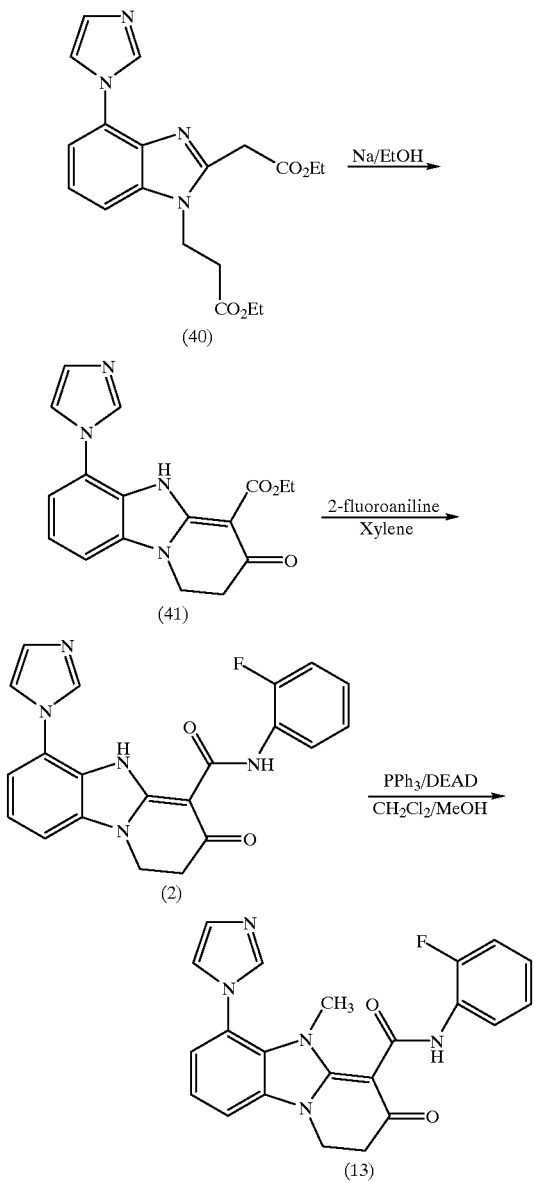

THF (500 mL) was shaken under 50 psig of hydrogen for 18 hrs. The suspension was filtered, and the filtrate concentrated to yield 38 as a syrup.

D. 1-(2-Cyanoethyl)-2-(ethoxycarbonylmethyl)-4-(1-imidazolyl)benzimidazole (39). Ethyl ethoxycarbonylacetimidate (29 g) was added to a solution of 38 (11 g, 0.048 mol) in ETOH (240 mL). The resultant solution was heated at reflux for 2.5 hrs and then allowed to sit at room temperature overnight. The solvent was removed, and the residue was dissolved in methylene chloride. The solution was washed with water, saturated aqueous NaCl, and concentrated to afford 39 as a white solid which was recrystallized from EtOH/water.

E. 1-[2-(Ethoxycarbonyl)ethyl]-2-(ethoxycarbonylmethyl)-4-(1-imidazolyl)benzimidazole (40). A solution of 39 (5.8 g) in 6N HCl/EtOH (8 mL) was stirred at room temperature for 6 hrs. The solution was concentrated, treated with water (1 mL), and neutralized with 15% NaOH/water to a pH of 10. The product was extracted into methylene chloride. The solution was dried (sodium sulfate), filtered, and concentrated to give 40 as a syrup.

F. Pyrido[1,2-a]benzimidazole-4-ethoxycarbonyl, 1,2,3,5-tetrahydro-3-oxo-6-(1-imidazolyl)-(41). A solution of 40 (5.3 g) and sodium (0.62 g) in ethanol (65 mL) was stirred at room temperature for 24 hrs. The solution was concentrated, treated with water (30 mL), neutralized with 1N HCl in water to a pH of 10, and solid precipitated. The precipitate was filtered to give 41. MS MH$^+$ 325.

G. Pyrido[1,2-a]benzimidazole-4-carboxamide, N-2-fluorophenyl-1,2,3,5-tetrahydro-3-oxo-6-(1-imidazolyl)-(2). A solution of 41 (1.20 g, 3.0 mmol) and 2-fluoroaniline (0.67 9) in xylenes (40 mL) was heated at reflux for 4 hrs. The solution was concentrated, treated with 6N HCl in EtOH, triturated with ether, and filtered to give an off-white solid which was recrystallized from 95% EtOH to give 2. MS MH$^+$ 390. $^1$H NMR (300 MHz, DMSO-d$_6$) δ 2.88 (t, 2H), 4.43 (t, 2H, J=5.14 MHz, J=6.0 MHz), 6.92–6.97 (m, 1H), 7.04–7.08 (m, 1H), 7.23 (m, 1H), 7.5 (m, 2H), 7.79 (s, 1H), 7.98 (s, 1H), 8.17 (s, 1H), 8.43 (t,1H), 9.53 (s, 1H), 12.18 (s,1H), 12.70 (s, 1H). Anal. calc'd for C$_{21}$H$_{16}$FN$_5$O$_2$.HCl.0.5H$_2$O: C, 58.00; H, 4.17; N, 10.19; H$_2$O, 2.07. Found: C, 57.91; H, 4.08; N, 16.02; H$_2$O, 1.04.

Compound 1 (see Table 1) was prepared in a similar manner using 2,6-difluoroaniline instead of 2-fluoroaniline in step G. Compound 17 was prepared in a similar manner using 2-aminothiazole instead of 2-fluoroaniline in step G.

EXAMPLE 5

Pyrido[1,2-a]benzimidazole-4-carboxamide, N-2-fluorophenyl-1,2,3,5-tetrahydro-3-oxo-6-(1-imidazolyl)-(#2)

A. 3-(1-Imidazolyl)-2-nitroaniline (36). Compound 25 (26.7 g, 0.154 mol) and imidazole (66 g, 0.97 mol) were heated together at 180° C. under nitrogen. After 18 hrs, water (400 mL) was added with stirring, the product extracted into methylene chloride and the solution was washed with saturated aqueous NaCl. The organic layer was concentrated to give 36 as an orange semi-solid. MS m/e 205 (MH$^+$).

B. 3-(1-Imidazolyl)-2-nitro-N-(2-cyanoethyl)aniline (37). A solution of 36 (10.6 g, 52 mmol), 40% Triton-B (1.37 mL, 40 mmol), and acrylonitrile (4.03 g, 76 mmol) in dioxane (170 mL) was stirred for 18 hrs at room temperature. The solution was then treated with ether (ca. 200 mL), and the precipitate was filtered to give 11.3 g of 37.

C. 3-(1-Imidazolyl)-2-amino-N-(2-cyanoethyl)aniline (38). Compound 37 (11.1 g) and palladium (10% Pd/C, 3 g) in

EXAMPLE 6

Pyrido[1,2-a]benzimidazole-4-carboxamide, N-2-fluorophenyl-1,2,3-trihydro-3-oxo5-methyl-6-(1-imidazolyl)-(#13)

MeOH (0.5 mL) was added to a solution of 2 free base (1.6 gm, 4.1 mmol), Ph$_3$P (3.23 gm, 12.3 mmol), DEAD (1.95 mL, 12.3 mmol) in CH$_2$Cl$_2$ (40 mL). The resultant solution was then stirred at room temperature overnight and the solvent was evaporated by vacuum. The crude product was purified by column chromatography (2% MeOH/CHCl$_3$) to give 13. MS MH$^+$ 404.0. $^1$H NMR (300 MHz, CDCl$_3$) δ 2.80 (t, 2H, J=6.00 MHz, J=5.14 MHz), 3.24 (s, 3H), 4.22 (t, 2H, J=5.14 MHz, J=6.0 MHz), 6.92–6.97 (m, 1H), 7.0–7.08 (m, 2H), 7.7 (s, 1H), 8.34 (t,1H, J=8.14 MHz, J=8.57 MHz), 11.79 (s, IH, NH). Anal. calc'd for C$_{22}$H$_{18}$N$_5$O$_2$F.2.7 HCl: C, 53.00; H, 4.13; N, 14.05; F, 3.81; Cl, 19.21. Found: C, 53.21; H, 4.23; N, 13.68; F, 3.69; Cl, 19.70.

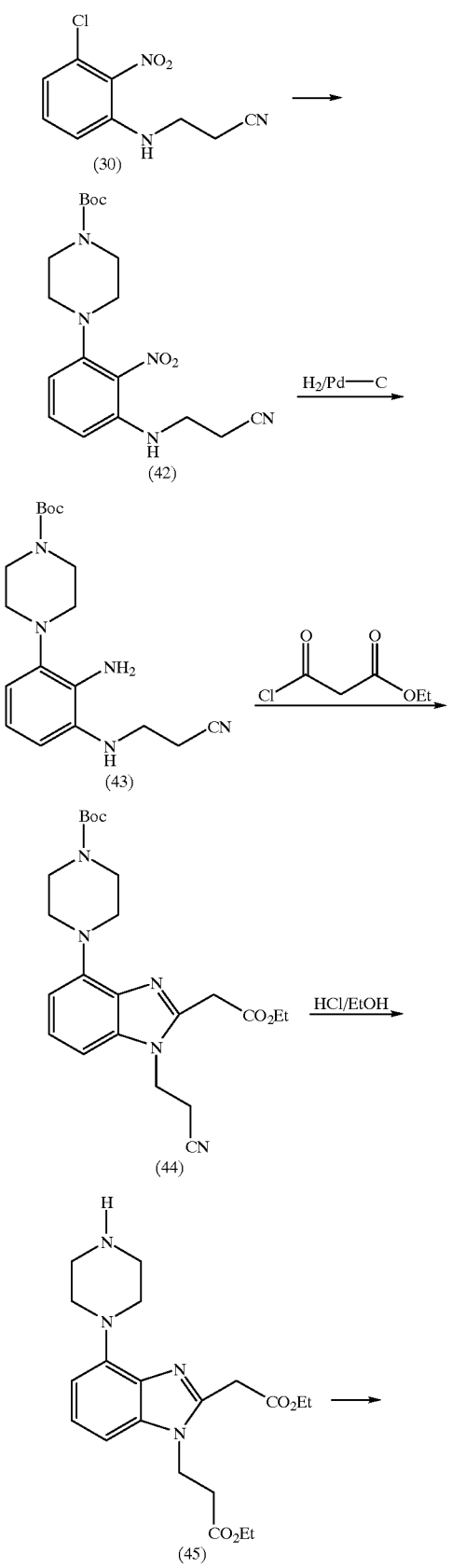
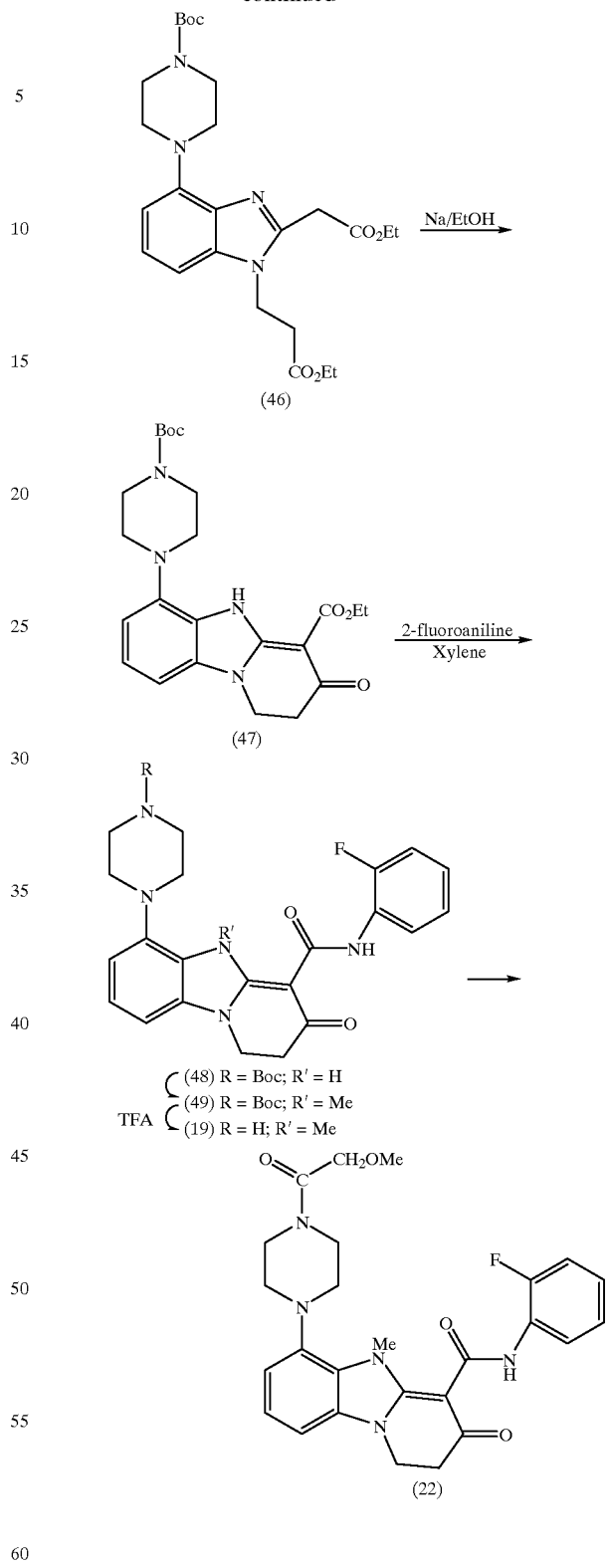
EXAMPLE 7
Pyrido[1,2-a]benzimidazole-4-carboxamide, N-(2-fluorophenyl)-1,2,3-trihydro-3-oxo-5-methyl-6-(1-piperazinyl)-(#19)
A. 3-(4-t-Butoxycarbonyl-1-piperazinyl)-2-nitro-N-(2-cyanoethyl)aniline (42). A mixture of 30 (3.50 g, 0.016 mol)

and t-butoxycarbonylpiperazine (5.77 g, 0.031 mol) was heated at 120° C. for 18 hrs, cooled, and dissolved in ethanol (100 mL) from which precipitated a yellow crystalline solid of 42 (MS MH$^+$ 376).

B. 3-(4-t-Butoxycarbonyl-1-piperazinyl)-2-nitro-N-(2-cyanoethyl)aniline (43). A solution of 42 (1.00 g, 0.003 mol) and 10% Pd-C catalyst (0.052 g) in En THF (15 mL) was shaken under 45–50 psig hydrogen for 48 hr. Filtration and evaporation gave a purple solid which was passed through flash silica (95/5 methylene chloride:methanol as eluant), to afford 43 as an off-white crystalline solid.

C. 1-(2-Cyanoethyl)-2-(ethoxycarbonylmethyl)-4-(4-t-butoxycarbonyl-1-piperazinyl)benzimidazole (44). A solution of 43 (2.20 g, 0.006 mol) and ethylmalonyl chloride (0.98 g, 0.007 mol) in ethyl acetate (20 mL) was refluxed overnight. Another 0.10 mL of ethylmalonyl chloride was added and the reaction was refluxed for 4 hr. After cooling, a light purple solid of 44 was filtered and isolated.

D. 1-[2-(Ethoxycarbonyl)ethyl]-2-(ethoxycarbonylmethyl)-4-( 1-piperazinyl)benzimidazole (45). A solution 44 (0.50g, 0.001 mol) in ethanol (25 mL) was treated with anhydrous HCl gas until the reflux ceased. The reaction mixture was refluxed for 15 min additionally, stirred at room temperature for 2 hr, and then evaporated. The residue was dissolved in water (3.0 mL), basified with 3N NaOH solution, and the solution was extracted with ethyl acetate. The organic phase was separated, dried, and evaporated to give diester 45 as a light colored oil.

E. 1-[2-(Ethoxycarbonyl)ethyl]-2-(ethoxycarbonylmethyl)-4-(4-t-butoxycarbonyl-1-piperazinyl)benzimidazole (46). A solution of 45 (0.68 g, 0.002 mol), di-t-butyl dicarbonate (0.47 g, 0.002 mol), water (3 mL), and dioxane (3 mL) was stirred at room temperature for 6 hr and then treated with methylene chloride (20 mL) and 3N NaOH with thorough mixing. The organic layer was separated, dried, and evaporated to give 46 as a yellow-orange oil (MS NH$^+$ 489).

F. Pyrido[1,2-a]benzimidazole-4-ethoxycarbonyl-1,2,3,5-tetrahydro-3-oxo-6-(4-t-butoxycarbonyl-1-piperazinyl)-(47). A solution of 46 (0.91 g, 0.002 mol) and ethanol (9 mL) was treated with sodium (0.17 g, 0.007 mol) and stirred overnight at room temperature. The ethanol was evaporated and water (5 mL) was added to the residue. After adjusting to pH 8 with 1N HCl, a solid of 47 formed which was collected by filtration (MS MH$^+$ 443.4).

G. Pyrido[1,2-a]benzimidazole-4-carboxamide, N-(2,6-difluorophenyl)-1,2,3,5-tetrahydro-3-oxo-6-(4-t-butoxycarbonyl-1-piperazinyl)-(48). Compound 47 (0.38 g, 0.0008 mol) was treated with 2-fluoroaniline (0.269 g, 0.002 mol) in xylene (5 mL) at reflux overnight. Filtration of the solid that precipitated afforded 48 as a cream-colored solid (MS MH$^+$ 508.4).

H. Pyrido[1,2-a]benzimidazole-4-carboxamide, N-(2-fluorophenyl)-1,2,3-trihydro-3-oxo-5-methyl6-(4-t-butoxycarbonyl-1-piperazinyl)-(49). A mixture of 48 (0.071 g, 0.0001 mol), methanol (0.0138 g, 0.0004 mol), triphenyl phosphine (0.108 g, 0.0004 mol), and THF (5 mL) was treated with diethylazodicarboxylate (0.072 g, 0.004 mol) and stirred at room temperature for 3 hr. The reaction mixture was evaporated to a residue which was passed through flash silica (95:5 methylene chloride:methanol) to give an oil. Diethyl ether was added causing a crystalline solid of 49 to form which was isolated by filtration (MS MH$^+$ 522.2)

I. Pyrido[1,2-a]benzimidazole-4-carboxamide, N-(2-fluorophenyl)-1,2,3-trihydro-3-oxo-5-methyl-6-(1-piperazinyl)-(19). Compound 49 (0.066 g, 0.0001 mol) was treated with trifluoroacetic acid (0.643 g, 0.006 mol) in methylene chloride (1 mL) at room temperature for 2 hr. The solvents were evaporated and the residue was dissolved in methylene chloride and mixed thoroughly with 3N NaOH. The organic layer was separated, dried and evaporated to give 0.050 g of a clear oil. This material was dissolved in ethanol and treated with fumaric acid (0.017 g). A crystalline fumarate solid formed which was isolated by filtration to give 19 as a white solid (MS MH$^+$ 422.5).

EXAMPLE 8

Pyrido[1,2-a]benzimidazole-4-carboxamide, N-2-fluorophenyl-1,2,3-trihydro-3-oxo-5-methyl-6-[4-(2-methoxyacetyl)-1-piperazinyl]-(#22)

A mixture of 19 (0.030 g, 0.07 mmol), N,N-diethylaminopropyl-Ni-ethyl-carbodiimide hydrochloride (0.027 g, 0.14 mmol), methoxyacetic acid (0.0064 g, 0.071 mmol), and methylene chloride (1 mL) was stirred at room temperature overnight. The reaction mixture was treated with 3N NaOH with vigorous stirring. The organic layer was separated, dried, and evaporated affording 22 as a solid (MS MH$^+$ 494.2).

The compounds of this invention were tested for affinity for the benzodiazepine sites of the GABA-A receptor. Since compounds which bind to this receptor can be useful in treating central nervous system disorders, the compounds were also tested in appropriate screens to evaluate specific activities. The results of the various screens are shown in Table 1.

Benzodiazepine Receptor Binding Assay

Selected compounds, which were prepared according to the experimental details given in the following examples, were tested for binding to the benzodiazepine site of the GABA-A receptor (Williams, M. et al., *J. Pharm. Exper. Therap.* 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand ($^3$H-flunitrazepam) was ca. 3 nM. Samples were incubated 10–20 min at 258C, after which the membrane material and bound ligand was collected on glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ value, for all tested compounds is listed in Table 1 in the fourth column from the right margin. An $IC_{50}$ value of over 10,000 for a particular compound would indicate that the compound was not active in this screen. This is a general screen and compounds active here have potential utility for the treatment of one or more disorders of the central nervous system.

Assay to Determine the Suppression of Metrazol-Induced Convulsions in Adult Male Mice Compounds of the invention were tested for their ability to reduce metrazol-induced convulsions in mice (Swinyard, E. A. *J. Am. Pharm Assoc.* 1949, 38, 201). Male $CD_1$ mice, were fasted at least 16 hours, were divided into equal groups and test compounds or vehicle were administered parenterally. Water was not withheld except during the period of observations. At the time of suspected peak activity, anti-pentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 mL/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. Probit Analysis, London: 1971, Cambridge University Press) and are listed in Table 1. An $ED_{50}$ value of greater than 30 indicates that an active dose for the compound being tested had not been determined. Compounds active in this screen are considered active anticonvulsion/antiepileptic agents, as well as having potential anxiolytic activity. The data for the test compounds is listed in Table 1 as Met. for either PO (oral) or IP (parenteral) routes of administration.

Assay to Measure the Suppression of Anxiety in the Adult Male Rat

The anxiolytic activity of selected compounds of the invention was assessed by determining their ability to release (disinhibit) behavior that had been suppressed by punishment (Vogel, J. R. et al. *Psychopharmacology* 1971, 21, 1). Male rats were deprived of water for 48 hrs and were deprived of food for 24 hrs prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase ($p<0.05$, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Table 1 under the heading Conf., with PO indicating an oral route of administration. The MED was defined as the minimum dose of the drug-treatment as analyzed using the Wilcoxon rank-sum test (SAS; Statistical Analysis System, version 5.16). If the MED value is greater than 10, an active dose of the compound being tested had not been determined.

TABLE 1

Biological activity of the compounds of formula 1 ($R_1$ = H, n = 1):

| Cpd # | MP (deg C) | MH+ MS | R3 | R2 | X | nM $IC_{50}$ | mg/kg Met. IP | mg/kg Met. PO | mg/kg Conf. PO |
|---|---|---|---|---|---|---|---|---|---|
| 1 | 226–230 | 408 | 2,6-$F_2$Ph | H | imidazol-1-yl | 0.66 | ≦1 | ~10 | ~3 |
| 2 | 242–244 | 390 | 2-FPh | H | imidazol-1-yl | 3.48 | 1 | ~5 | >10 |
| 3 | 268–271 | 409 | 2-FPh | H | morpholin-4-yl | 1.05 | >1 | 3 | >10 |
| 4 | 211–213 | 427 | 2,6-$F_2$Ph | H | morpholin-4-yl | 0.23 | <1 | <3 | ~0.1 |
| 5 | 179–182 | 532 | 2,6-$F_2$Ph | H | 1-(2-methoxyphenyl)-piperazin-4-yl | <100 | | | >10 |
| 6 | 232–235 | 514 | 2-FPh | H | 1-(2-methoxyphenyl)-piperazin-4-yl | ~1000 | | | >10 |
| 7 | 215–218 | 421 | 4-(MeO)Ph | H | morpholin-4-yl | 2.04 | | | 0.1 |
| 8 | 173–174 | 421 | 3-(MeO)Ph | H | morpholin-4-yl | 2.4 | | | >10 |
| 9 | 273–275 | 407 | 2-FPh | H | piperidin-1-yl | 69.5 | | | ≦3 |
| 10 | 238–240 | 425 | 2,6-$F_2$Ph | H | piperidin-1-yl | 0.41 | | 3.64 | 3 |
| 11 | 229–231 | 419 | 4-(MeO)Ph | H | piperidin-1-yl | 34.8 | | | >3 |
| 12 | 237–238 | 423 | 2-FPh | Me | morpholin-4-yl | 0.15 | | | |
| 13 | 191.5–192.5 | 404 | 2-FPh | Me | imidazol-1-yl | 0.13 | | | >3 |
| 14 | 275–276 | 425 | 2-FPh | H | thiomorpholin-4-yl | 8.43 | | | ~3 |
| 15 | 147–148 | 439 | 2-FPh | Me | thiomorpholin-4-yl | 0.23 | | | 1 |
| 16 | 217–218 | 393 | thiazol-2-yl | Me | imidazol-1-yl | 2.12 | | | >3 |
| 17 | 273.5 dec | 379 | thiazol-2-yl | H | imidazol-1-yl | 160 | | | >3 |
| 18 | 155–158 | 421 | 2-FPh | Me | piperidin-1-yl | 0.22 | | 0.65 | .03–.1 |
| 20 | 263 dec | 465 | 2-FPh | H | 1,4-dioxo-8-azaspiro-[4,5]decan-8-yl | 1.11 | | 0.83 | 3 |
| 21 | 135 | 479 | 2-FPh | Me | 1,4-dioxo-8-azaspiro-[4,5]decan-8-yl | 0.13 | | | ≦0.3 |

TABLE 1-continued

Biological activity of the compounds of formula 1 ($R_1$ = H, n = 1):

| Cpd # | MP (deg C) | MH+ MS | R3 | R2 | X | nM IC$_{50}$ | mg/kg Met. IP | mg/kg Met. PO | mg/kg Conf. PO |
|---|---|---|---|---|---|---|---|---|---|
| 22 | | 494 | 2-FPh | Me | 1-(2-methoxyacetyl)-piperazin-4-yl | 0.24 | | | >3 |
| 23 | 190–191 dec | 421 | 2-FPh | H | 4-piperidinon-1-yl | <1000 | | | ≦3 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

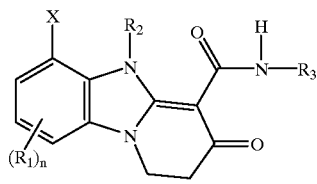

wherein:
each $R_1$ is independently selected from the group consisting of hydrogen; $C_{1-8}$alkyl; halogen; perfluoro$C_{1-4}$alkyl; hydroxy; $C_{1-4}$alkoxy; di($C_{1-4}$alkyl)amino; amino; amino($C_{1-8}$)alkylamino; nitro; $C_{1-4}$alkoxycarbonyl; and $C_{1-4}$alkylthio;

$R_2$ is selected from the group consisting of hydrogen; $C_{1-6}$alkyl; aralkyl; heteroaryl$C_{1-4}$alkyl; $(R_4)_2N(CH_2)_p$ wherein $R_4$ is the same or different and are independently selected from H, $C_{1-4}$alkyl, aralkyl, aryl or substituted aryl wherein the substituents are independently selected from $C_{1-4}$alkyl, $C_{1-4}$alkoxy, nitro, amino or halo; or $R_4$ together with the nitrogen form a heterocyclic ring selected from piperidinyl, pyrrolidinyl, morpholinyl, thiomorpholinyl, piperazinyl, imidazolyl, pyrazolyl, triazolyl, indolyl; indolinyl, benzimidazolyl, pyrrolyl and indazolyl; $R_5O(CH_2)_p$ and $R_5S(CH_2)_p$ wherein $R_5$ is selected from $C_{1-4}$alkyl, aralkyl, aryl or substituted aryl wherein the substituents are independently selected from $C_{1-4}$alkyl, $C_{1-4}$alkoxy, nitro, amino or halo; and p is an integer from 1–5;

$R_3$ is selected from the group consisting of aryl; substituted aryl wherein the substituents are independently selected from $C_{1-8}$alkyl, halo, perfluoro$C_{1-4}$alkyl, hydroxy, $C_{1-4}$alkoxy, amino, nitro, di($C_{1-4}$alkyl)amino, $C_{1-4}$alkoxycarbonyl, amino$C_{2-6}$alkoxy, $C_{1-8}$alkylamino$C_{2-6}$alkoxy, di ($C_{1-8}$alkyl) amino$C_{2-6}$alkoxy or $C_{1-4}$alkylthio; a heteroaryl ring selected from pyridyl; thiazolyl; thiophenyl; furyl; indolyl; benzothiophenyl; pyridazinyl; pyrimidinyl; indolyl; imidazolyl; indolinyl; quinolinyl; indazolyl; benzofuryl; triazinyl; pyrazinyl; isoquinolinyl; isoxazolyl; thiadiazolyl; benzothiazolyl; triazolyl; and benzotriazolyl; a substituted heteroaryl ring wherein the substituents are independently selected from oxo, halo, perfluoro$C_{1-4}$alkyl, amino, nitro, $C_{1-4}$alkylthio, $C_{1-4}$alkoxy, $C_{1-4}$alkylamino, di ($C_{1-4}$alkyl) amino, carboxy or $C_{1-4}$alkoxycarbonyl; and cycloalkyl having 3-8 carbon atoms;

X is a heterocyclic or carbocyclic ring selected from the group consisting of piperidinyl, pyrrolidinyl, morpholinyl, thiomorpholinyl, piperazinyl, imidazolyl, pyrazolyl, pyridinyl, pyrazinyl, pyrimidinyl, pyridazinyl, thiazolyl, isothiazolyl, oxazolyl, isoxazolyl, oxazolinyl, triazolyl, tetrazolyl, oxadiazolyl, dioxaazaspirodecanyl, thiadiazolyl, purinyl, benzimidazolyl, benzothiophenyl, benzothiazolyl, indolyl; cyclo($C_{3-8}$)alkyl; phenyl; and naphthyl; a substituted heterocyclic, carbocyclic, or aryl ring wherein the substituents are independently selected from $C_{1-8}$alkyl, halogen, perfluoro$C_{1-4}$alkyl, hydroxy, amino, nitro, oxo, $C_{1-4}$-alkoxy, $C_{1-4}$alkylamino, di($C_{1-4}$alkyl)amino, $C_{1-4}$alkoxycarbonyl, $C_{1-4}$alkoxy$C_{1-4}$alkylcarbonyl, aryl, substituted aryl wherein the substituents are independently selected from $C_{1-4}$alkyl, $C_{1-4}$alkoxy, nitro, amino or halo; heteroaryl; or $C_{1-4}$alkylthio; and
n is an integer from 1–3;
or pharmaceutically acceptable salts thereof.

2. A compound of claim 1 wherein $R_1$ is hydrogen or $C_{1-8}$alkyl; $R_2$ is H, $C_{1-6}$alkyl, $(R_4)_2N(CH_2)_p$, $R_5O(CH_2)_p$, or $RS(CH_2)_p$; $R_3$ is aryl, substituted aryl, a heteroaryl ring or a substituted heteroaryl ring; X is aryl, substituted aryl, a heterocyclic ring, a substituted heterocyclic ring, a carbocyclic ring or a substituted carbocyclic ring; n is 1–3 and p is 1–5.

3. The compound of claim 1 wherein $R_1$ is H; $R_2$ is H or $C_{1-6}$alkyl; $R_3$ is aryl, haloaryl, $C_{1-4}$alkoxyaryl or heteroaryl; and X is a heterocyclic ring.

4. The compound of claim 3 wherein X is a heterocyclic ring selected from imidazol-1-yl; morpholin-4-yl; alkoxyphenylpiperazin-4-yl; piperidin-1-yl; thiomorpholin-4-yl; piperazin-1-yl; 1,4-dioxo-8-azaspiro[4,5]decan-8-yl; 1-(2-methoxyacetyl)piperazin-4-yl and piperidinon-1-yl.

5. The compound of claim 1 wherein $R_1$ is H; $R_2$ is H or $C_{1-6}$alkyl; $R_3$ is aryl, haloaryl, $C_{1-4}$alkoxyaryl or heteroaryl; and X is a carbocyclic ring.

6. The compound of claim 5 wherein the carbocyclic ring is a phenyl ring.

7. The compound of claim 1 wherein $R_1$ is H, $C_{1-8}$alkyl or halo; $R_2$ is H, $C_{1-6}$alkyl, heteroaryl, $R_5O(CH_2)_p$, $R_5S(CH_2)_p$ or $(R_4)N(CH_2)_p$; $R_3$ is phenyl or substituted phenyl; a heteroaryl ring or a substituted heteroaryl ring; and X is a heterocyclic or a carbocyclic ring.

8. The compound of claim 1 wherein $R_1$ is hydrogen, $R_2$ is hydrogen or $C_{1-6}$alkyl; $R_3$ is phenyl, substituted phenyl, a heteroaryl ring or a substituted heteroaryl ring and X is a heterocyclic or carbocyclic ring.

9. The compound of claim 1 wherein:

each $R_1$ is independently selected from the group consisting of hydrogen; $C_{1-8}$alkyl; halogen; perfluoro$C_{1-4}$alkyl; hydroxy; $C_{1-4}$alkoxy; di($C_{1-4}$alkyl)amino; amino; amino$C_{1-8}$alkylamino; nitro; $C_{1-4}$alkoxycarbonyl; and $C_{1-4}$alkylthio;

$R_2$ is selected from the group consisting of hydrogen; $C_{1-6}$alkyl; phenyl ($C_{1-4}$) alkyl; heteroaryl ($C_{1-4}$) alkyl; $(R_4)_2N(CH_2)_p$ wherein $R_4$ is the same or different and are independently selected from hydrogen, $C_{1-4}$alkyl, benzyl, phenyl or substituted phenyl wherein the substituent is $C_{1-4}$alkyl, $C_{1-4}$alkoxy, nitro, amino or halo; or $R_4$ together with the nitrogen form a heterocyclic ring; $R_5O(CH_2)_p$ wherein $R_5$ is selected from $C_{1-4}$alkyl, benzyl, phenyl or substituted phenyl wherein the substituent is selected from $C_{1-4}$alkyl, $C_{1-4}$alkoxy, nitro, amino or halo; and $R_5S(CH_2)_p$ wherein $R_5$ is selected from $C_{1-4}$alkyl, benzyl, phenyl or substituted phenyl wherein the substituent is selected from $C_{1-4}$alkyl, $C_{1-4}$alkoxy, nitro, amino or halo; and p is 1–5;

$R_3$ is independently selected from the group consisting of phenyl; substituted phenyl, wherein the substituents are independently selected from $C_{1-8}$alkyl, halo, perfluoro$C_{1-4}$alkyl, hydroxy, $C_{1-4}$alkoxy, amino, nitro, di($C_{1-4}$alkyl)amino, $C_{1-4}$alkoxycarbonyl or $C_{1-4}$alkylthio; a heteroaryl ring; a substituted heteroaryl ring; and cycloalkyl having 3–8 carbon atoms;

X is a heterocyclic ring, a substituted heterocyclic ring, a carbocyclic ring or a substituted carbocyclic ring.

10. The compound of claim 1 wherein $R_1$ is H; $R_2$ is H or $C_{1-6}$alkyl; $R_3$ is selected from 2,6-difluorophenyl, 2-fluorophenyl, 4-methoxyphenyl, 3-methoxyphenyl and thiazol-2-yl; and X is selected from imidazol-1-yl, morpholin-4-yl, 1-(2-methoxyphenyl)piperazin-4-yl; piperidin-1-yl; thiomorpholin-4-yl; 1,4-dioxo-8-azaspiro(4,5)decan-8-yl; 1-(2-methoxyacetyl)piperazin-4-yl and 4-piperidinon-1-yl.

11. A compound of claim 1 selected from the group consisting of:

pyrido[1,2-a]benzimidazole-4-carboxamide, N-(2,6-difluorophenyl)-1,2,3,5-tetrahydro-3-oxo-6-(1-piperidinyl)-;

pyrido[1,2-a]benzimidazole-4-carboxamide, N-2-fluorophenyl-1,2,3,5-tetrahydro-3-oxo-6-[8-(1,4-dioxa-8-azaspiro[4,5]decanyl)]-;

pyrido[1,2-a]benzimidazole-4-carboxamide, N-2-fluorophenyl-1,2,3,5-tetrahydro-3-oxo-1-(4-oxopiperidinyl)-;

pyrido[1,2-a]benzimidazole-4-carboxamide, N-2-fluorophenyl-1,2,3-trihydro-3-oxo-5-methyl-6-[8-(1,4-dioxa-8-azaspiro[4,5]decanyl)]-;

pyrido[1,2-a]benzimidazole-4-carboxamide, N-2-fluorophenyl-1,2,3,5-tetrahydro-3-oxo-6-(1-imidazolyl)- ;

pyrido[1,2-a]benzimidazole-4-carboxamide, N-2-fluorophenyl-1,2,3-trihydro-3-oxo-5-methyl-6-(1-imidazolyl)- ;

pyrido[1,2-a]benzimidazole-4-carboxamide, N-(2-fluorophenyl)-1,2,3-trihydro-3-oxo-5-methyl-6-(1-piperazinyl)- ; and pyrido[1,2-a]benzimidazole-4-carboxamide, N-2-fluorophenyl-1,2,3-trihydro-3-oxo-5-methyl-6-[4-(2-methoxyacetyl)-1-piperazinyl]-;

or pharmaceutically acceptable salts thereof.

12. A compound of the formula:

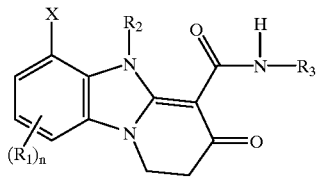

wherein:

each $R_1$ is independently selected from the group consisting of hydrogen; alkyl-(C1–8); halogen; perfluoro $C_{1-4}$alkyl; hydroxy; $C_{1-4}$ alkoxy; di($C_{1-4}$alkyl)amino; amino; aminoalkylamino; nitro; $C_{1-4}$ alkoxycarbonyl; and $C_{1-4}$alkylthio;

$R_2$ is selected from any of hydrogen; alkyl ($C_{1-6}$); aryl ($C_{1-4}$)alkyl; heteroaryl($C_{1-4}$)alkyl; $(R_4)_2N(CH_2)_p$ wherein $R_4$ is the same or different and is independently selected from H, ($C_{1-4}$)alkyl, aralkyl, aryl and substituted aryl wherein the substituents are independently selected from ($C_{1-4}$)alkyl, ($C_{1-4}$)alkoxy, nitro, amino and halo; or $R_4$ together with the nitrogen form a heterocyclic ring selected from piperidinyl, pyrrolidinyl, morpholinyl, thiomorpholinyl, piperazinyl, imidazolyl, pyrazolyl, triazolyl, indolyl; indolinyl, benzimidazolyl, pyrrolyl and indazolyl; $R_5O(CH_2)_p$ and $R_5S(CH_2)_p$ wherein $R_5$ is selected from ($C_{1-4}$)alkyl, aralkyl, aryl, and substituted aryl wherein the substituents are independently selected from ($C_{1-4}$)alkyl, ($C_{1-4}$)alkoxy, nitro, amino, and halo; and p is an integer from 1–5;

$R_3$ is selected from the group consisting of aryl; substituted aryl wherein the substituents are independently selected from $C_{1-8}$alkyl, halo, perfluoro$C_{1-4}$alkyl, hydroxy, $C_{1-4}$alkoxy, amino, nitro, di$C_{1-4}$alkylamino, $C_{1-4}$alkoxycarbonyl, and $C_{1-4}$alkylthio; a heteroaryl ring selected from pyridyl; pyridyl-N-oxide; thiazolyl; thiophenyl; furyl; indolyl; benzothiophenyl; pyridazinyl; pyrimidinyl; indolyl; indolinyl; quinolinyl; indazolyl; benzofuryl; triazinyl; pyrazinyl; isoquinolinyl; isoxazolyl; thiadiazolyl; benzothiazolyl; triazolyl; and benzotriazolyl; a substituted heteroaryl ring wherein the substituents are independently selected from halo, perfluoro$C_{1-4}$alkyl, amino, nitro, $C_{1-4}$alkylthio, $C_{1-4}$alkoxy, $C_{1-4}$alkylamino, di$C_{1-4}$dialkylamino, carboxy and $C_{1-4}$alkoxycarbonyl; and cycloalkyl having 3–8 carbon atoms;

X is a heterocyclic or carbocyclic ring selected from the group consisting of piperidinyl, pyrrolidinyl, morpholinyl, thiomorpholinyl, piperazinyl, imidazolyl, pyrazolyl, pyridinyl, pyrazinyl, pyrimidinyl, pyridazinyl, thiazolyl, isothiazolyl, oxazolyl, isoxazolyl, oxazolinyl, triazolyl, tetrazolyl, oxadiazolyl, dioxaazaspirodecanyl, thiadiazolyl, purinyl, benzimidazolyl, benzothiophenyl, benzothiazolyl, indolyl; cyclo($C_{3-8}$)alkyl; phenyl; and naphthyl; a substituted heterocyclic, carbocyclic, or aryl ring wherein the substituents are independently selected from alkyl($C_{1-8}$), halogen, perfluoroCl-4alkyl, hydroxy, amino, nitro, oxo, $C_{1-4}$-alkoxy, mono- and di-($C_{1-4}$ alkyl)amino, $C_{1-4}$alkoxycarbonyl, $C_{1-4}$alkoxy ($C_{1-4}$)alkylcarbonyl, aryl, substituted aryl wherein the substituents are independently selected from $(C_{1-4})$alkyl, $(C_{1-4})$alkoxy, nitro, amino, and halo; heteroaryl; and $C_{1-4}$alkylthio; and n is an integer from 1–3;

or pharmaceutically acceptable salts thereof.

13. A pharmaceutical composition comprising a therapeutically effective amount of a compound of claim 1 and a pharmaceutically acceptable carrier.

14. A pharmaceutical composition made by mixing a compound of claim 1 and a pharmaceutically acceptable carrier.

15. A process for making a pharmaceutical composition comprising mixing a compound of claim 1 and a pharmaceutically acceptable carrier.

16. A method of treating disorders of the central nervous system comprising administering to a mammal in need of such treatment a therapeutically effective amount of a compound of claim 1.

17. The method of claim 16, wherein the therapeutically effective amount is from about 0.2 to about 25 mg/kg per day.

18. The method of claim 16 wherein the disorder is selected form the group consisting of anxiety, convulsions, depression, sleeplessness, muscle spasm, ADHD and benzodiazepine drug overdose.

* * * * *